United States Patent [19]
Schafer

[11] Patent Number: 5,613,493
[45] Date of Patent: Mar. 25, 1997

[54] ULTRASONIC APPARATUS AND METHOD FOR MEASURING ANIMAL BACKFAT

[76] Inventor: Mark E. Schafer, 165 Percy Ct., Norristown, Pa. 19401

[21] Appl. No.: 533,359

[22] Filed: Sep. 25, 1995

[51] Int. Cl.$^6$ ........................................................ A61B 8/00
[52] U.S. Cl. ................................ 128/660.06; 128/661.03
[58] Field of Search ........................ 128/660.01, 660.06, 128/660.07, 661.02, 661.03; 73/627, 629

[56] References Cited

U.S. PATENT DOCUMENTS

| | | | |
|---|---|---|---|
| 4,646,748 | 3/1987 | Fujii et al. ........................... | 128/660.06 |
| 4,785,817 | 11/1988 | Stouffer ................................ | 128/660.06 |
| 5,353,796 | 10/1994 | Schroeder et al. .................. | 128/660.01 |
| 5,520,183 | 5/1996 | Lake et al. ........................... | 128/660.06 |

*Primary Examiner*—George Manuel
*Attorney, Agent, or Firm*—John Shaw Stevenson

[57] ABSTRACT

An ultrasonic measuring apparatus and method to accurately determine the depth of an overlaying backfat on an animal without incurring any damage to the animal. The apparatus employs a reverse time analysis approach in which a pulse generator sends a preselected ultrasonic input signal by way of a piezoelectric transducer through the outer skin and successively through each one of the animal's fat layer interfaces to a preselected distance within the loin portion of the animal. This reverse time approach then analyzes the resulting echo signal produced by the input signal sequentially in a direction from this loin portion toward the outer fat layers and the first strong signal within a specified range, which depends on the species, breed, age or weight of the animal to be measured, is taken as the bottom most fat-loin transition. A microprocessor is employed to measure and analyze the amplitude and contour of this signal in a direction toward the loin until it reaches a fixed point that is a prescribed percentage of the peak value of the amplitude of this signal the magnitude of which depends on the type of animal under measurement. The value derived in this manner is an accurate measurement of the depth of overlaying backfat and is automatically displayed in digital form on a screen.

10 Claims, 4 Drawing Sheets

ULTRASONIC APPARATUS AND METHOD FOR MEASURING ANIMAL BACKFAT

BACKGROUND OF THE INVENTION

1. Field of the Invention

The present invention employs a unique ultrasound apparatus to more accurately determine the maximum backfat in any one of a variety of animals even though the number and thickness of their backfat layers are different because of their different species, breeds, ages and weights. As meat packers make their profits from selling lean meat, it is vital for them to purchase live animals; e.g. pigs, that contain a minimal amount of backfat. It is therefore vital that they employ an apparatus that will more accurately measure the backfat of the animals they purchase than those backfat measuring apparatus that are presently available for this purpose.

2. Description of the Prior Art

Prior art backfat measuring devices have used a single ultrasonic beam known as A-mode technology and swept beam known as B-mode technology. Prior A-mode methods have used simple peak detection and peak counting techniques of the echo signals generated by the fat layers of livestock to determine the total depth of their fat cover. The advantage of A-mode is its lower cost and lower system complexity. Existing systems have also used visual user interpretation of the signal waveforms. B-mode systems have used user interpretation, or some automated means involving lateral pattern recognition. However, B-mode systems with this feature currently require an external computer interface and analysis equipment. Therefore, these B-mode systems are too costly and too complex to satisfy present-day purchasers of such equipment. Present day A-mode systems fail to completely solve this problem because when an input signal is transmitted into the backfat of an animal the resulting amplitude of the reflected peak of the signal that is detected by present day techniques are often in error due of the variability of the tissue reflection strength, causing either false returns if the detection level is too low, or missed returns if the peak detection threshold is too high. Further, in most livestock species, especially pork, the number of fat layers increases with increasing fat thickness. Therefore a peak-counting procedure can be in error. In addition, the final tissue interface between fat and muscle, which is the most important one in terms of fat thickness measurement, is generally not a distinct, thin layer, but an extended region of connective tissue. The peak of the ultrasound signal returned from this type of layer does not adequately quantify the extent of the layer, which leads to errors unacceptable in the present-day market.

Prior art, for example Carlson (U.S. Pat. Nos. 4,359,055 and 4,359,056), uses peak detection circuitry to find the location of the peak of each echo signal returned as a result of ultrasonic pulses that have been transmitted into the animal through a transducer. However, there is an error in this approach because this approach identifies the peak of the echo signal as the depth to the fat/loin interface, whereas the true fat/loin interface is at a substantial percentage below the peak. The fact that the fat/loin interface is below the peak was shown to be true in an accreditation test by the National Swine Improvement Federation in January 1995. The federation certified operators using the system disclosed herein which uses this below-the-peak measurement approach to have a high degree of accuracy in backfat measurements when compared to actual carcass data.

SUMMARY OF THE INVENTION

The object of this invention is to employ an apparatus and method that uses ultrasound signals reflected from layers of backfat within livestock animals; e.g. swine, cattle, sheep, to accurately determine the depth of the fat layer, by properly accounting for the nature of the fat/loin interface within the animal which vary with the animal's species, breed and weight. Neither is this apparatus as disclosed herein subject to errors in the measurement of the depth of the fat layers as the number of fat layers change in an animal with increasing age. The prior art approaches consider the reflection time signal strength history of using a reflected signal as a function of receive time using forward time analysis. In other words, decisions are made with regard to the interface positions starting from the transducer and proceeding further into the animal when using these prior art devices. On the other hand, the present invention uses a reverse time approach in which the signal is analyzed from deeper to shallower depths of fat, and the first strong signal within a specified range, such range to be dependent upon the animal to be measured, is taken as the bottommost fat/loin layer transition. This is the fat to loin transition. This removes the ambiguity which arises when there are different layers of fat as a function of animal's age, weight and fat characteristics. Once the signal which corresponds to the deepest fat layer is so identified, the location of the deeper edge of the signal, not the location of its peak, is taken as the fat/loin interface. This is because the tissues which make up the fat/loin interface are not well defined, and produce indistinct echo patterns rather than sharply defined peaks. Therefore, the reflection must be considered an extended time signal, and the true interface between fat and loin is found at the trailing, or deeper edge of the signal. The deeper edge location derived from experimental research is defined as that point which is proportionally lower than the peak. For example, the point on the trailing edge of the signal which is 30% of the peak value was determined by experimentation to represent the true fat/lean interface of swine. This 30% level on which this trailing edge is located is shown in FIG. 4 of the drawing as the Threshold Level.

DETAILED DESCRIPTION OF THE INVENTION

Figure 1:
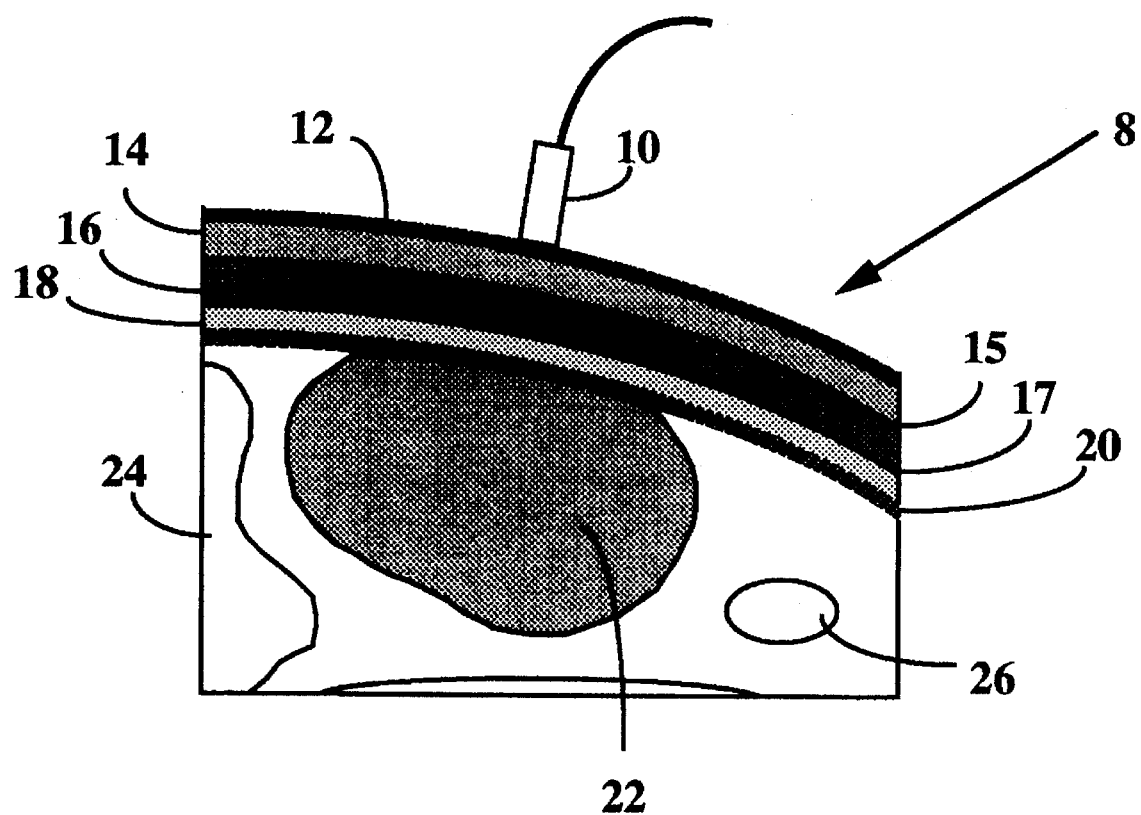
FIG. 1 is a sectional view through a portion of the animal's back with the transducer probe in place.

FIG. 1 shows a typical cross sectional view of the backfat and loin of an animal such as a hog 8. The ultrasound transducer 10 is applied to the outer intact skin surface 12 of the animal, with a coupling fluid such as oil. The transducer emits and receives ultrasound pulses which reflect from the various tissue layers within the animal. The first fat layer 14 is typically six to ten millimeters in depth and is separated from the second fat layer 16 by a thin membrane 15. Similarly, the second and third backfat layers 16 and 18 are separated by a thin membrane 17. The third or additional backfat layers only appear in certain species and breeds and at certain ages and weights Thus the number and thicknesses of the different fat layers can change significantly from one animal to another, from one breed to another and by species. The border between the last fat layer 18 and the beginning of the loin muscle 22 is denoted as 20. FIG. 1 shows backbone 24 and rib bone 26 which can be used to provide orientation of the loin muscle. The invention accurately quantifies the depth to the beginning of the loin muscle 22 or, in other words, the bottom of the interface 20 by analyzing the ultrasound signals reflected back to transducer 10.

Figure 2:
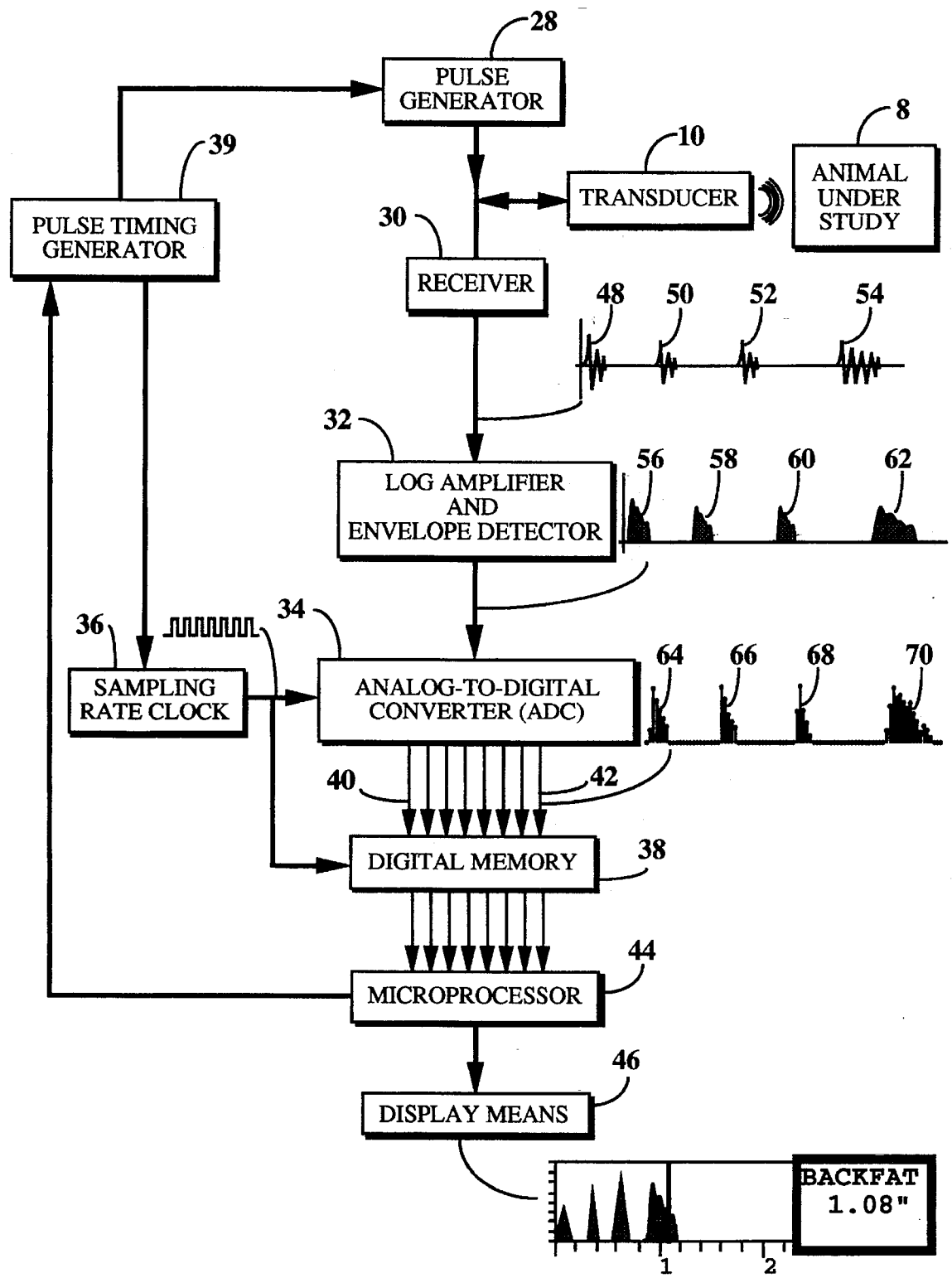
FIG. 2 is a flow diagram which shows the components of the present invention.
Figure 3:
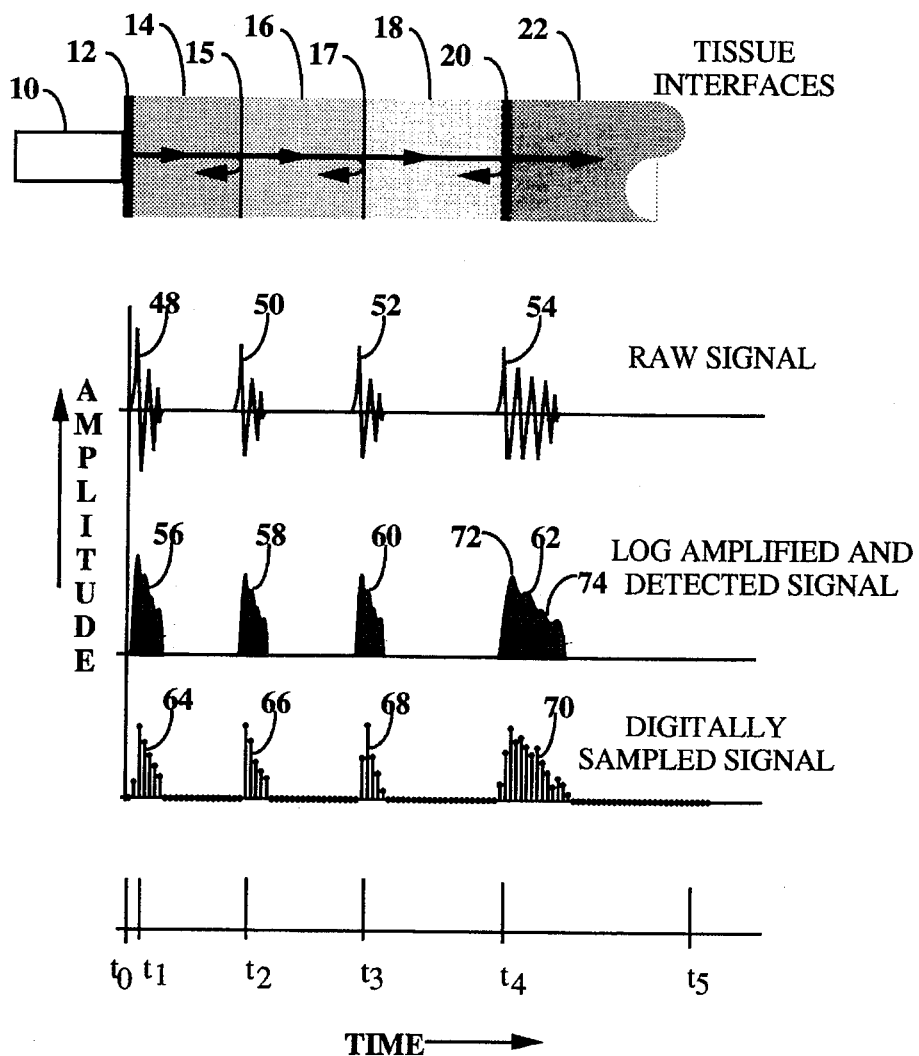
FIG. 3 shows an arrow indicating an ultrasonic input signal transmitted through backfat and the fat/loin interface and how the responding output signals are modified by the system components over various time response periods.

FIG. 2 shows an apparatus to accurately quantify the depth to the beginning of the aforementioned loin muscle 22 or, in other words, the bottom of the interface 20 by analyzing the ultrasonic signal reflected back to transducer 10. This FIG. 2 shows the components for executing the principles of this invention. A pulse generator 28 is used to excite the ultrasound transducer 10. The transducer 10 emits an A-mode ultrasound wave into the tissue and this ultrasound energy in the form of an echo signal is reflected back to the transducer 10 at each tissue interface 15, 17, 20 which are shown in FIG. 1 and 3. The signals received at the transducer 10 is amplified by receiving circuits 30. The received signals are logarithmically amplified and enveloped by detector 32 before being converted into a fully digital form by the analog to digital converter, ADC, 34. The sampling rate of the ADC 34 is set by a clock circuit 36 which establishes the temporal resolution of the system. Since in this type of system, travel time of the ultrasonic wave is related to travel distance, the clock 36 also sets the spatial resolution of the system. The time duration of the transmitted pulse is thus also a factor of the spatial resolution. The clock circuit 36 also sequences the digital memory circuit 38. The clock is started at the same time as the transmitting pulse so there is proper time synchronization. The exact number of clock cycles and thus the size of the digital memory circuit 38 depends upon the sampling rate and the desired depth of tissue to be measured. FIG. 2 shows a number of electrical connections; e.g., 40, 42 between the ADC 34 and the digital memory 38 to represent the number of bits and resolution of the ADC. At least six bits of resolution are required and eight bits are generally desired in utilizing this system. Because the clock 36 is synchronized with the pulse generator 28 and the clocking frequency is known, then each sample within the digital memory 38 corresponds to a specific time from the time of the ultrasonic waveform. Thus, each sample within the digital memory corresponds to a specific depth within the fat layers forming the backfat of the animal. The depth and the time are related by the speed of sound in the backfat which is generally taken at 1540 meters per second.

Once a single received waveform is stored in the digital memory 38 it is read and analyzed using the microprocessor 44 which can be for example a 8051 family of microcontrollers; for instance, the DS80C320 from Dallas Semiconductor. The microprocessor 44 drives a display means 46 which communicates the results of the measurements to the user. The display is a full graphic display of the waveform and may be implemented using a graphic LCD display such as the HG 24501 from Hyundai Electronics.

Figure 4:
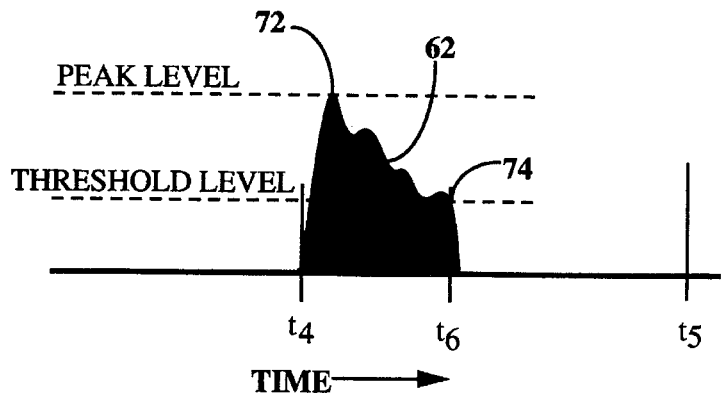
FIG. 4 shows in graphic form how the apparatus of FIG. 2 can precisely determine the backfat of an animal.

In order to explain further how the apparatus functions, reference is now made to FIG. 3. The trace shown in the upper portion of FIG. 3 represents the received ultrasound signals 48, 50, 52 and 54 as a function of time as produced by the receiver circuit 30 as a result of the signal it receives from the transducer 10. The trace shown in the lower portion of FIG. 3 shows the log amplified and detected signals 56, 58, 60 and 62 correspond to the reflection of the interface between the animal's skin 12 and fat layer 14 and interfaces 15, 17 and 20 respectively as shown in FIG. 1. After logarithmic amplification and detection, the signals which correspond to 48, 50, 52 and 54 are 56, 58, 60 and 62 respectively which in turn are then converted into the digitally sampled signals 64, 66, 68 and 70 shown in FIG. 3. It can be seen that the signals 54 and 62 are of extended time duration relative to the other signals. FIG. 4 shows how to repeatedly and reliably determine the extent of signal 62 and thus, the exact point of the beginning of the loin muscle 22 or, in other words, the depth of maximum backfat at interface 20 as shown in FIG. 1. The apparatus as shown in FIG. 2 thus correctly identifies the signal which corresponds to interface 20 irrespective the number of intervening fat layers.

FIG. 4 further shows an expanded view of the signal 62 and time interval $t_4$ to $t_5$. The apparatus shown in FIG. 2 starts by examining the signal in reverse time order; that is, from $t_5$ to $t_4$ as shown in FIG. 3. Time $t_5$ is selected by previous experimentation for the specific species of animal to be measured and is such that it will always be located at a point beyond the deepest fat thickness of that species. Experimental research has determined that for market hogs in the weight of two hundred to two hundred eighty pounds, the deepest backfat thickness is 2.4 inches and therefore, this $t_5$ as shown in FIG. 3 is set to a time corresponding to 2.5 inches. Starting at time $t_5$ in FIG. 3 and working toward time $t_0$, the echo signal 62 becomes the first echo, thus removing the ambiguity caused by the variability in the number of echoes such as 58 and 60. The apparatus shown in FIG. 2 next performs a search for a peak of the echo signal 62 and finds the point labeled 72 as identified in FIG. 4. Once this point 72 is located and this peak level is found, the apparatus of FIG. 2 next searches back in the direction of $t_5$ until the signal level falls below a threshold level as indicated by reference numeral 74. This threshold level is taken as a percentage of the peak level. In this way, variations in the absolute signal level are not important since the threshold is always set as a percentage of the peak level. The particular percentage of the peak level employed for hogs has been found through experimentation to be 30%. This percentage was found to best represent the true fat/muscle interface when compared to actual carcass data measurements.

Figure 5:
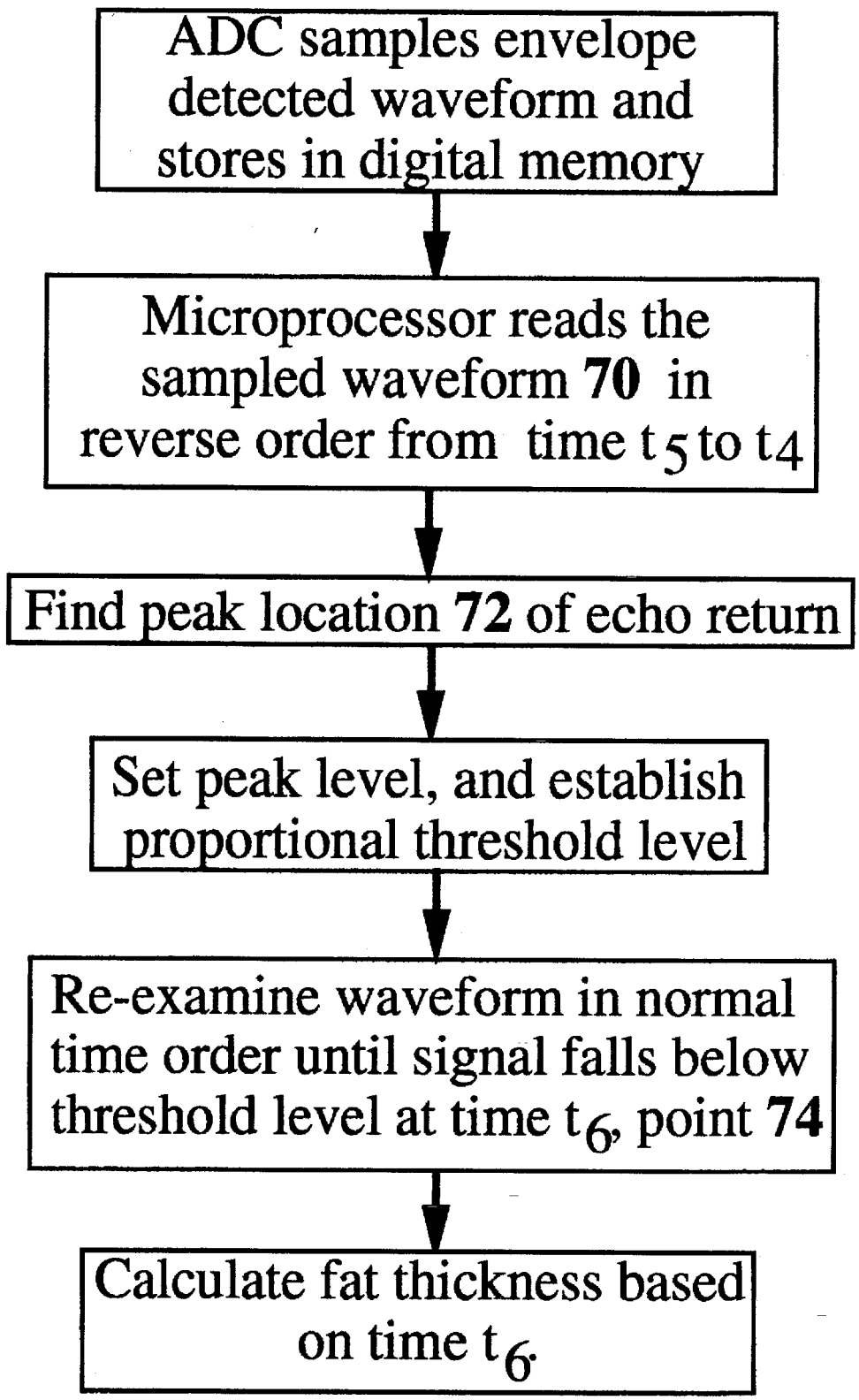
FIG. 5 shows the sequential steps the apparatus of FIG. 2 takes in very accurately determining the backfat of an animal.

FIG. 5, which is self-explanatory, shows the most important steps in the order of execution which components of the apparatus shown in FIG. 2 employs to obtain the maximum amount of backfat in an animal.

Summarizing, it can be seen that the use of the aforementioned unique reverse time approach for measuring the depth of backfat of an animal is preferred over any other animal backfat measuring device that is presently available because:

(a) It has been tested, shown and accepted in meat producer tests to produce the most accurate measurement of backfat of any of the backfat measuring devices that are presently available.

(b) Meat packers with this measuring device will be able to more accurately select for purchase animals which possess a minimal amount of backfat and they will therefore experience a greater return on their investment due to less fat waste when they dress these animals for consumer use;

(c) Because this reverse time backfat depth measuring system is constructed to take into account changes in the nature of the fat/loin interface in an animal due to its species, breed and weight, a more accurate measure of the depth of the backfat of an animal is achieved than prior art backfat measuring devices because they are not designed to compensate for these changes.

(d) This reverse time backfat depth measuring system is unique because it first identifies the peak level of the echo response signal representative of the deepest fat layer adjacent the fat/loin interface of the animal. It then moves downward along the trace of this signal to identify a point on a threshold level that is located at a fixed preset percent of the peak; e.g., 30% for swine and will therefore accurately measure the depth of animal backfat though the tissues that make up the fat/loin interface which is not as well defined as other fat interfaces. This reverse system is used to measure the depth of backfat by using this threshold level measuring technique and has in practice been shown to be a much more accurate measurement of the depth of backfat in an animal than prior devices that use the amplitude of peak echo response signals per se.

(e) The system disclosed herein provides numerous depth of fat measurements in a more accurate and more stable manner over a long period of time than prior art devices.

What is claimed is:

1. A system using a reverse time approach to accurately measure and indicate the thickness of backfat in an animal comprising a means to transmit a digital control signal to a pulse timing generator which synchronizes the transmitting and receiving functions of the system, said generator being operable to convert said digital control signal into a high voltage excitation, a transducer connected to said generator to convert said last mentioned signal into an ultrasonic wave and to transmit said wave signal through the outer skin and backfat of said animal and then off of the backfat/loin interface, a receiver to amplify the responding ultrasonic echo signal reflected from the backfat/loin interface and to convert said echo signal back to an electrical signal, a log amplifier and envelope detector to further amplify said last mentioned electrical signal in a logarithmic manner, an analog to digital converter to convert said last mentioned signal into a digital signal, a sample rate clock to regulate the rate by which said last mentioned signal is sampled by the analog to digital converter, said clock being connected to a pulse timing generator for synchronization therewith and to a microprocessor by way of a digital memory circuit, said microprocessor being operable to measure the peak of said last mentioned signal that is representative of the maximum amplitude of the response signal that is generated by said fat/loin interface, said microprocessor being further operable to select a prescribed point on the trace of said responding signal that is below said peak that represents an accurate measurement of the depth of backfat and a display means operably connected to said microprocessor for visually indicating the thickness of backfat in said animal.

2. The apparatus of claim 1 wherein the animal is a member of the swine family and the prescribed point on said trace of said responding signal that is below said peak of the signal that is selected is 30% of the value of the amplitude of said peak signal.

3. The apparatus of claim 1 wherein the ultrasonic beam is an single A-mode beam.

4. The system according to claim 1 wherein a piezoelectric transducer with oil as a coupling fluid is employed to transmit said input signal and to receive the said responding signal.

5. The system according to claim 1 wherein the loin of the animal into which the input signal is transmitted is in close proximity to the fat/loin interface.

6. The system according to claim 1 wherein a full graphic LCD display of said waveform is employed to indicate the depth of said backfat.

7. The system according to claim 1 wherein the animal is a hog weighing between 200 and 280 pounds and wherein the distance between the skin and fat/loin interface for all animals in this category is a maximum distance of 2.4 inches and the selected distance through which the input signal is allowed to be sent into the loin of the animal is 2.5 inches as measured from the outer skin of the animal.

8. A reverse time system to accurately measure the depth of backfat in an animal comprising, an electrical means to send an ultrasonic input signal of a predetermined time duration through the skin of an animal that will extend through its backfat into a loin portion thereof and then in a reverse direction of its backfat/loin interface regardless of the species, breed, age, weight or number of fat layers the animal possesses, a control means to sense the amplitude of the peak of a response signal that is generated by said backfat/loin interface and to follow the trace of said response signal to a point on the trace that is of a predetermined percentage of the amplitude of the peak that is related to any of the aforementioned characteristics of the animal, and means to convert a waveform representing the time value of the point on the trace into a measurement of the depth of backfat possessed by the animal.

9. The system according to claim 8 wherein the animal is a member of the swine family and said predetermined percentage of said peak for said swine is 30% and wherein the selected percentage of the amplitude of said peak is predetermined by experimental research on animals regardless of the species, breed, age, weight or number of fat layers.

10. A method of accurately measuring the depth of the backfat in an animal comprising the steps of:

(a) Transmitting an ultrasonic input signal through the backfat and loin interface of an animal;

(b) Sampling the responding echo waveform from the backfat/loin interface using an analog-to-digital converter and storing it in a digital memory;

(c) Reading the sampled echo waveform in reverse order first from the loin and then toward the fat/loin interface;

(d) Locating the peak location of the responding sampled echo waveform generated by said interface;

(e) Selecting a prescribed percentage of the peak that is characteristic of the type of animal under measurement;

(f) Tracing the waveform in normal forward time order and in a downward direction from the peak until it reaches a point on the trace that is a prescribed percentage of the amplitude of the peak; and (g) Determining the thickness of backfat in an animal based on the response time corresponding to the point on said trace where it falls below the prescribed percentage of said peak.

* * * * *